United States Patent
Rossignol et al.

(10) Patent No.: US 9,351,937 B2
(45) Date of Patent: May 31, 2016

(54) CONTROLLED RELEASE PHARMACEUTICAL FORMULATIONS OF NITAZOXANIDE

(71) Applicant: Romark Laboratories L.C., Tampa, FL (US)

(72) Inventors: Jean-Francois Rossignol, St. Petersburg, FL (US); Marc Ayers, Tampa, FL (US)

(73) Assignee: Romark Laboratories L.C., Tampa, FL (US)

( * ) Notice: Subject to any disclaimer, the term of this patent is extended or adjusted under 35 U.S.C. 154(b) by 247 days.

(21) Appl. No.: 13/954,184

(22) Filed: Jul. 30, 2013

(65) Prior Publication Data

US 2014/0065215 A1     Mar. 6, 2014

Related U.S. Application Data

(62) Division of application No. 12/656,704, filed on Feb. 12, 2010, now Pat. No. 8,524,278.

(60) Provisional application No. 61/202,285, filed on Feb. 13, 2009.

(51) Int. Cl.

| | | |
|---|---|---|
| *A01N 25/32* | (2006.01) |
| *A61K 9/20* | (2006.01) |
| *A61K 9/24* | (2006.01) |
| *A61K 9/28* | (2006.01) |
| *A61K 31/426* | (2006.01) |
| *A61K 31/7056* | (2006.01) |
| *A61K 38/21* | (2006.01) |

(52) U.S. Cl.
CPC .............. *A61K 9/2086* (2013.01); *A61K 9/209* (2013.01); *A61K 9/28* (2013.01); *A61K 9/284* (2013.01); *A61K 9/2853* (2013.01); *A61K 31/426* (2013.01); *A61K 31/7056* (2013.01); *A61K 38/21* (2013.01)

(58) Field of Classification Search
CPC .... A61K 9/2086; A61K 9/209; A61K 31/426
See application file for complete search history.

(56) References Cited

U.S. PATENT DOCUMENTS

| | | | |
|---|---|---|---|
| 3,950,351 A | 4/1976 | Rossignol et al. | |
| 5,387,598 A | 2/1995 | Rossignol et al. | |
| 5,578,621 A | 11/1996 | Rossignol | |
| 5,886,013 A | 3/1999 | Rossignol | |
| 5,968,961 A | 10/1999 | Rossignol | |
| 6,117,894 A | 9/2000 | Rossignol | |
| 7,285,567 B2 | 10/2007 | Rossignol | |
| 7,709,022 B2 | 5/2010 | Kanikanti et al. | |
| 2006/0024365 A1* | 2/2006 | Vaya et al. .................. 424/468 |
| 2006/0141037 A1 | 6/2006 | Mehta et al. | |
| 2007/0015803 A1 | 1/2007 | Rossignol | |
| 2007/0167504 A1 | 7/2007 | Rossignol | |
| 2008/0096941 A1 | 4/2008 | Rossignol | |
| 2008/0097106 A1 | 4/2008 | Rossignol | |
| 2008/0299188 A1 | 12/2008 | Appel et al. | |
| 2009/0036467 A1 | 2/2009 | Rossignol et al. | |

FOREIGN PATENT DOCUMENTS

| | | |
|---|---|---|
| CN | 1438889 A | 8/2003 |
| EP | 0923934 B1 | 8/2003 |
| JP | 2005-538121 A | 12/2005 |
| WO | WO 00/25752 A1 | 5/2000 |
| WO | WO 02/26214 A1 | 4/2002 |
| WO | WO 03/026637 A2 | 4/2003 |
| WO | WO 2004/012713 A1 | 2/2004 |
| WO | WO 2005/013935 A2 | 2/2005 |
| WO | WO 2007/020337 A1 | 2/2007 |

OTHER PUBLICATIONS

Chilukuri et al., Application No. 21-497 21-498/S-001, Clinical Pharmacology and Biopharmaceutics Review(s), Jul. 14, 2014, http://www.accessdata.fda.gov/drugsatfda_docs/nda/2004/21-497_Alinia_BioPharmr.pdf, 35 pages.

* cited by examiner

*Primary Examiner* — Johann R Richter
*Assistant Examiner* — Danielle Sullivan
(74) *Attorney, Agent, or Firm* — Foley & Lardner LLP

(57) ABSTRACT

Solid dosage formulations of nitazoxanide or a nitazoxanide analog are provided that comprise a controlled release portion and an immediate release portion. The pharmaceutical composition is typically in the form of a bilayer solid oral dosage form comprising (a) a first layer comprising a first quantity of nitazoxanide or analog thereof in a controlled release formulation; and (b) a second layer comprising a second quantity of nitazoxanide or analog thereof in an immediate release formulation. Method of using the formulations in the treatment of hepatitis C are also provided.

20 Claims, No Drawings

CONTROLLED RELEASE PHARMACEUTICAL FORMULATIONS OF NITAZOXANIDE

CROSS-REFERENCE TO RELATED APPLICATIONS

This application is a divisional of U.S. application Ser. No. 12/656,704, filed Feb. 12, 2010, now U.S. Pat. No. 8,524,278, which claims priority to U.S. Provisional Application No. 61/202,285, filed Feb. 13, 2009, the entire contents of which are incorporated herein by reference.

BACKGROUND

Nitazoxanide (2-(acetolyloxy)-N-(5-nitro-2-thiazolyl) benzamide) is a compound having the following structure:

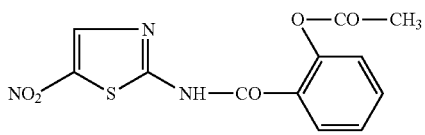 [SMILES: CC(=O)Oc1ccccc1C(=O)Nc1ncc([N+](=O)[O-])s1]

The preparation and uses of this compound are disclosed, for example, in U.S. Pat. No. 3,950,351 to Rossignol.

Pharmaceutical compositions containing nitazoxanide and its metabolite, tizoxanide, were originally developed and marketed for treating intestinal parasitic infections.

Following oral administration of nitazoxanide or mixtures of nitazoxanide plus tizoxanide in humans, these compounds are partially absorbed from the intestinal tract, and nitazoxanide is rapidly hydrolyzed to form tizoxanide in plasma. Tizoxanide is glucurono-conjugated, and the drug is eliminated in urine and bile as tizoxanide or tizoxanide glucuronide. The half-life of tizoxanide in plasma is only approximately 1.5 hours.

For treating intestinal infections, pharmaceutical compositions containing nitazoxanide or mixtures of nitazoxanide and tizoxanide and a wetting agent and optionally a starch derivative have been used successfully. The use of particles of active ingredients ranging between 5 and 200 µm was shown to be important to achieving safety and efficacy. The use of a pharmaceutically acceptable acid has been shown to improve the stability of these pharmaceutical compositions. See, for example, U.S. Pat. Nos. 5,387,598; 5,968,961; and 6,117,894 to Rossignol. Tablet and suspension formulations have been shown to be equally effective for treating intestinal parasitic infections regardless of their relative bioavailability.

The absorption of nitazoxanide and nitazoxanide-tizoxanide mixtures from the intestinal tract varies significantly depending on the pharmaceutical formulation. For example, the relative bioavailability of an oral suspension has surprisingly been shown to be only 70% of that of a tablet. Systemic bioavailability of these compounds has not been of paramount importance, however, because the compounds have been used almost exclusively for treating parasites that reside in the lumen of the intestinal tract or in the intestinal mucosa.

Nitazoxanide and tizoxanide have also been shown to be active in vitro against certain DNA viruses in vitro (see, for example, U.S. Pat. Nos. 5,578,621 and 5,886,013, to Rossignol). In recent years, they were surprisingly shown to have activity against hepatitis C virus (HCV), an RNA virus, in vitro and in clinical trials (Reference pending US application, "Viral Hepatitis Treatment"). The mechanism of action of nitazoxanide and tizoxanide in inhibiting virus replication is not known, but it has been postulated to be a "cell-mediated" mechanism because of its broad spectrum antiviral activity and the inability to induce resistance.

Early clinical trials of nitazoxanide and tizoxanide in treating chronic hepatitis C were conducted using a tablet formulation developed for treatment of intestinal parasitic infections. That tablet contained 500 mg of active ingredient (99% nitazoxanide/1% tizoxanide). In patients chronically infected with HCV genotype 4, sustained virologic response (SVR) rates of 61% to 80% were achieved when the tablets were administered one tablet twice daily for 4 to 12 weeks followed by the same regimen plus standard doses of peginterferon α-2a with or without ribavirin for 36 weeks. By contrast, patients treated with the standard therapy, peginterferon α-2a plus ribavirin for 48 weeks, experienced only a 50% SVR rate.

While early trials in patients with chronic hepatitis C genotype 4 showed improved efficacy using the 500 mg tablet, a significant number of patients were not cured. Higher doses of active ingredient could not be used to improve efficacy because previous studies have shown that doses of 1000 mg twice daily are associated with a significant increase in side effects, which are primarily related to the intestinal tract (e.g., abdominal pain, diarrhea and nausea). These side effects reduce patient compliance with the treatment regimen and are particularly unacceptable for long-term treatment of patients with hepatitis C.

For treating chronic HCV infection, tizoxanide must be delivered into the bloodstream and to the infected hepatocytes. Ideally, the drug should be administered by oral route no more often that twice daily and without significant side-effects in order to maximize the adherence of patients to the treatment regimen.

The variable absorption of nitazoxanide and tizoxanide in different dosage formulations, the very short half-life of tizoxanide in plasma and side-effects associated with high doses of nitazoxanide and tizoxanide in the intestinal tract are problems that must be overcome in developing a new optimized dosage formulation for treating chronic hepatitis C. Furthermore, because the mechanism of action of nitazoxanide against HCV is unknown, it is impossible to know whether fluctuations in peak and trough concentrations at the site of infection are beneficial or detrimental to improving efficacy.

Thus, there is a need for a solid dosage formulation of nitazoxanide and/or tizoxanide with improved efficacy in treating chronic hepatitis C compared to tablets described in the prior art, and without any increase in side effects.

SUMMARY

Controlled release formulations of nitazoxanide and nitazoxinide analogues are described, as well as method of using the formulations in the treatment of hepatitis C. In particular, solid dosage formulations of nitazoxanide and nitazoxinide analogues are described that comprise a controlled release portion and an immediate release portion.

Thus, in some aspects, a pharmaceutical composition in the form of a solid dosage form is provided, the composition comprising (a) a first portion comprising a first quantity of nitazoxanide or an analogue thereof in a controlled release formulation; and (b) a second portion comprising a second quantity of nitazoxanide or an analogue thereof in an immediate release formulation. In some embodiments, the composition is a solid oral dosage form in the form of a tablet or, in other embodiments, in the form of a capsule.

In other aspects, a method is provided for treating a patient suffering from hepatitis C, the method comprising administering to the patient a therapeutically effective amount of a pharmaceutical composition in the form of a solid dosage form, the composition comprising (a) a first portion comprising a first quantity of nitazoxanide or an analogue thereof in a controlled release formulation; and (b) a second portion comprising a second quantity of nitazoxanide or an analogue thereof in an immediate release formulation.

In yet other aspects, a method is provided for treating a patient suffering from hepatitis C, the method comprising (i) pretreating the patient by administering to the patient for a period of time a first composition in the form of a solid oral dosage form comprising nitazoxanide or an analogue thereof as a first active agent, wherein the first composition comprises (a) a first portion comprising a first quantity of nitazoxanide or analogue thereof in a controlled release formulation, and (b) a second portion comprising a second quantity of nitazoxanide or analogue thereof in an immediate release formulation; and (ii) after the period of time in (i), administering to the patient a second composition comprising a therapeutically effective amount of a second active agent.

In some aspects, a method is provided for reducing one or more side-effects associated with treatment with nitazoxanide or tizoxanide in a patient, the method comprising administering to the patient a therapeutically effective amount of a pharmaceutical composition in the form of a solid dosage form, the composition comprising (a) a first portion comprising a first quantity of nitazoxanide or an analogue thereof in a controlled release formulation; and (b) a second portion comprising a second quantity of nitazoxanide or an analogue thereof in an immediate release formulation.

In other aspects, a method is provided for increasing the bioavailability of nitazoxanide or an analogue thereof in a patient, the method comprising administering to the patient a therapeutically effective amount of a pharmaceutical composition in the form of a solid dosage form, the composition comprising (a) a first portion comprising a first quantity of nitazoxanide or an analogue thereof in a controlled release formulation; and (b) a second portion comprising a second quantity of nitazoxanide or an analogue thereof in an immediate release formulation.

In other aspects, a method is provided for extending absorption of nitazoxanide or an analogue thereof in a patient, the method comprising administering to the patient a therapeutically effective amount of a pharmaceutical composition in the form of a solid dosage form, the composition comprising (a) a first portion comprising a first quantity of nitazoxanide or an analogue thereof in a controlled release formulation; and (b) a second portion comprising a second quantity of nitazoxanide or an analogue thereof in an immediate release formulation.

In yet other aspects, a controlled release tablet for oral administration is provided, the tablet comprising nitazoxanide or an analogue thereof and a low-viscosity polymer, wherein the low-viscosity polymer controls the release of the nitazoxanide or analogue thereof.

DETAILED DESCRIPTION

The present compositions are controlled release solid formulations of nitazoxanide or nitazoxanide analogues, in particular, controlled release solid oral dosage forms comprising (a) a first portion comprising a first quantity of nitazoxanide or an analogue thereof in a controlled release formulation; and (b) a second portion comprising a second quantity of nitazoxanide or an analogue thereof in an immediate release formulation. The formulations are typically in the form of a bilayer tablet for oral administration. The compositions can be used to effectively treat chronic hepatitis C and provide increased bioavailability and better absorption of nitazoxanide, with fewer of the side effects commonly seen in standard nitazoxanide formulations.

Unless otherwise specified, "a" or "an" means "one or more."

As used herein, the term "controlled release" refers to a property of a pharmaceutical composition wherein the absorption and bioavailability of the active agent in the composition is maintained such that therapeutically effective amounts of the active agent are bioavailable over an extended period of time.

As used herein, the term "immediate release" refers to a property of a pharmaceutical composition wherein the active agent in the composition is made bioavailable without substantial delay.

As used herein the terms "treating" and "treatment" refer to a reduction in severity and/or frequency of symptoms, elimination of symptoms and/or underlying cause, prevention of the occurrence of symptoms and/or their underlying cause (e.g., prophylactic therapy), improvement or remediation of damage, or reduction in intensity of infection.

By the terms "effective amount" and "therapeutically effective amount" of a compound of the invention is meant a nontoxic but sufficient amount of the compound to provide the desired effect.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The present solid compositions can comprise two portions, each containing a quantity of nitazoxanide of nitazoxanide analogue. Thus, in some embodiments, the compositions comprise a first portion that contains nitazoxanide or analogue in a controlled release formulation, and a second portion contains nitazoxanide analogue in an immediate release formulation. In some embodiments, the solid composition is in the form of a tablet in which the immediate release portion is in the form of a layer that is deposited on top of the controlled release portion, and compressed to form a tablet. The solid dosage form can also be in the form of a capsule containing both controlled release granules and immediate release granules.

The present formulations contain nitazoxanide or an analogue thereof as the active agent. Methods of preparing nitazoxanide are known in those skilled in the art. See, e.g., U.S. Pat. No. 3,950,351 to Rossignol. Examples of nitazoxanide analogues and methods of preparing them are disclosed in U.S. Pat. Nos. 7,285,567 and 6,117,894, and in published U.S. patent application nos. 2007/0167504, 2007/0015803, 2008/0097106, 2008/0096941, and 2009/0036467. Each of these U.S. patents and publications are incorporated by reference herein in their entireties.

As used herein, the term "nitazoxanide" refers to both nitazoxanide (2-(acetolyloxy)-N-(5-nitro-2-thiazolyl)benzamide) and to a nitazoxanide analogue, e.g., to one of the compounds disclosed in U.S. Pat. No. 7,285,567 or US 2007/0167504.

Nitazoxanide or any of the nitazoxanide analogues may be administered in the form of the compound per se, and/or, where suitable, in the form of a salt, polymorph, ester, amide, prodrug, derivative, or the like, provided the salt, polymorph, ester, amide, prodrug or derivative is suitable pharmacologically. Such salts, esters, amides, prodrugs and other derivatives of these active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any nitazoxanide analogue active agents that may exist in enantiomeric forms, the active agent may be incorporated into the present compositions either as the racemate or in enantiomerically enriched form.

The total amount of nitazoxanide in the present compositions is typically about 60% to 75% by weight of the composition. In those embodiments having controlled release and immediate release portions, the quantity of nitazoxanide in the controlled release portion is typically greater than the quantity in the immediate release portion, with the ratio of the quantity of nitazoxanide in the controlled release portion to the nitazoxanide in the immediate release portion being about 2.5-4.0:1. For example, in some embodiments, the controlled release portion contains about 500 mg of nitazoxanide, and the immediate release portion contains about 175 mg of nitazoxanide. In other embodiments, the controlled release portion contains about 250 mg of nitazoxanide, and the immediate release portion contains about 87.5 mg of nitazoxanide.

The compositions can contain one or more additional pharmaceutically acceptable additives or excipients. In those embodiments with controlled release and immediate release portions, both the controlled release portion and the immediate release portion can contain one or more additional pharmaceutically acceptable additives or excipients. These excipients are therapeutically inert ingredients that are well known and appreciated in the art. As used herein, the term "inert ingredient" refers to those therapeutically inert ingredients that are well known in the art of pharmaceutical science, which can be used singly or in various combinations, and include, for example, diluents, disintegrants, binders, suspending agents, glidants, lubricants, fillers, coating agents, solubilizing agent, sweetening agents, coloring agents, flavoring agents, and antioxidants. See, for example, Remington: The Science and Practice of Pharmacy 1995, edited by E. W. Martin, Mack Publishing Company, 19th edition, Easton, Pa.

Examples diluents or fillers include, but are not limited to, starch, lactose, xylitol, sorbitol, confectioner's sugar, compressible sugar, dextrates, dextrin, dextrose, fructose, lactitol, mannitol, sucrose, talc, microcrystalline cellulose, calcium carbonate, calcium phosphate dibasic or tribasic, dicalcium phosphaste dehydrate, calcium sulfate, and the like.

Diluent(s) or filler(s) typically represent about 10% to 15% by weight of the controlled release or immediate release portion, or about 2% to about 15% by weight of the entire composition.

Examples of disintegrants include, but are not limited to, alginic acid, methacrylic acid DVB, cross-linked PVP, microcrystalline cellulose, sodium croscarmellose, crospovidone, polacrilin potassium, sodium starch glycolate, starch, including corn or maize starch, pregelatinized starch and the like.

Disintegrant(s) typically represent about 10% to 15% by weight of the controlled release or immediate release portion, or about 2% to about 15% by weight of the entire composition.

Examples of binders include, but are not limited to, starches such as potato starch, wheat starch, corn starch; microcrystalline cellulose; celluloses such as hydroxypropyl cellulose, hydroxyethyl cellulose, hydroxypropylmethyl cellulose (HPMC), ethyl cellulose, sodium carboxy methyl cellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, and the like.

Binder(s) typically represent about 2% to 15% by weight of the controlled release or immediate release portion, or about 0.2% to about 14% by weight of the entire composition.

Examples of glidants include, but are not limited to, silicon dioxide, colloidal anhydrous silica, magnesium trisilicate, tribasic calcium phosphate, calcium silicate, magnesium silicate, colloidal silicon dioxide, powdered cellulose, starch, talc, and the like.

Glidant(s) typically represent about 0.1% to 0.5% by weight of the controlled release or immediate release portion, or about 0.01% to about 0.3% by weight of the entire composition.

Examples of lubricants include, but are not limited to, magnesium stearate, aluminum stearate, calcium stearate, zinc stearate, stearic acid, polyethylene glycol, glyceryl behenate, mineral oil, sodium stearyl fumarate, talc, hydrogenated vegetable oil and the like.

Lubricant(s) typically represent about 0.5% to 1.5% by weight of the controlled release or immediate release portion, or about 0.2% to about 1.0% by weight of the entire composition.

For example, in some embodiments, the controlled release portion, the immediate release portion, or both contain a starch as the diluent, such as corn or maize starch; sodium croscarmellose and the disintegrant; hydroxypropylcellulose, microcrystalline cellulose, and/or hydroxypropyl methylcellulose and the binder(s); dicalcium phosphate dehydrate as the filler; colloidal anhydrous silica as the glidant; and magnesium stearate as the lubricant.

The present controlled release compositions also contains a binder that is a low-viscosity polymer. Examples of low-viscosity polymers include, but are not limited to, low-viscosity hydroxypropyl methylcellulose polymers such as those sold by Dow Chemical under the tradename "Methocel®" (e.g., Methocel E50LV®, Methocel K100LV®, and Methocel F50LV®) and low-viscosity hydroxyethylcellulose polymers. The low-viscosity polymer controls the release of the nitazoxanide or analogue thereof in the formulation.

The low-viscosity polymer is typically present at about 10% to about 20%, or about 10% to about 15%, or preferably about 12%, of the total weight of the entire composition, or, in those embodiments having controlled release and immediate release portions, the low-viscosity polymer in the controlled release portion is typically present at about 15% to about 20%, preferably about 18%, of the weight of the controlled release portion.

The present compositions can further comprise a coating material. The coating material is typically present as an outer layer on the dosage form that completely covers the formulation. For example, in some embodiments, the dosage form is an oral tablet in which the controlled release portion forms a first layer of the tablet and the immediate release portion forms a second layer that is deposited on top of the first layer to form a core tablet. In such embodiments, e.g., the coating material can be in the form of an outer coating layer that is deposited on top of the core tablet.

The coating material typically is about 1% to about 5% by weight of the composition.

The coating material can comprise hydroxypropylmethylcellulose and/or polyethylene glycol, and can comprise one or more excipients selected from the group comprising coating agents, opacifiers, taste-masking agents, fillers, polishing agents, coloring agents, antitacking agents and the like. For example, the coating material can contain titanium dioxide as an opacifying agent. Examples of film-coating substances and methods for using such coating substances are well known to those of skill in the art.

For example, the coating material used in the present compositions can be OPADRY AMB 80W91416 or OPADRY FX 63F97546, as in the examples below.

Methods of making solid pharmaceutical formulations are known to those of skill in the art of pharmaceutical formulations and can be employed to prepare the present compositions. See, for example, *Remington*: The Science and Practice of Pharmacy (1995), edited by E. W. Martin, Mack Publishing Company, 19th edition, Easton, Pa.

The present compositions can be used to effectively treat chronic hepatitis C and provide increased bioavilability and better absorption of nitazoxanide, with fewer of the side effects commonly seen in standard nitazoxanide formulations.

The compositions may be administered for any length of time suitable for effective for treatment of hepatitis C. Any appropriate dosage and regimen may be used for the compositions. Administration can typically be carried out over a period of about 3 days to about 104 weeks, but may be carried out over a period longer than 104 weeks and may even be carried out indefinitely. For example, treatment of hepatitis C using the present formulations will typically involve administration of the formulations over a period of 12, 24, or 48 weeks. Appropriate regimens can be determined by a physician.

One or more additional active agents may be included in the present pharmaceutical compositions and methods of treatment. For example, in some embodiments, the compositions may include one or more additional therapeutic agents useful in treating hepatitis C such as ribavirin, and immune-stimulating agents including, but not limited to, interferons such as interferon $\alpha$-2b, a derivative of interferon $\alpha$-2b such as a polyethylene glycol-conjugated form of interferon $\alpha$-2b, interferon $\alpha$-2a, or interferon alfacon-1.

The composition and the additional active agent (e.g., an interferon) may be administered simultaneously, or separately, at the same time, or in different compositions (including in separate compositions that vary in dosage form, release profiles, and the like).

For example, in some embodiments, a patient suffering from hepatitis C is first pretreated with one of the nitazoxanide compositions described herein. The duration of the pretreatment period may be between about 3 days and about 6 months, for example, between about 1 week and about 12 weeks, and, as a further example, between about 1 week and about 4 weeks. The pretreatment period can be followed subsequently by a treatment period wherein the pretreated patient is treated with either an interferon alone or an interferon plus nitazoxanide and, optionally, one or more additional agents such as an antiviral agent, e.g., ribavirin. Any of the interferons described herein may be used during the treatment period. The duration of the treatment period can be any duration that is required to obtain the desired response, and will typically be between about 1 day and about 12 months or longer. For example, the treatment period may comprise weekly injections of an interferon, and may involve a single week of treatment, 2-4 weeks of treatment, 4-12 weeks of treatment, or more (such as 6 months, 1 year, 2 years, or indefinitely).

It is to be understood that the description above as well as the examples that follow are intended to illustrate and not limit the scope of the invention. Other aspects, advantages and modifications within the scope of the invention will be apparent to those skilled in the art to which the invention pertains.

EXAMPLES

Example 1

Factors Affecting Bioavailability of Nitazoxanide

A study was performed to investigate the impact of each of the following factors on bioavailablity of nitazoxanide: (1) absorption of tizoxanide vs. nitazoxanide, (2) modifying site of release in GI tract, (3) effect of different polymers, and (4) effect of granulation in alcohol vs. water.

Six different nitazoxanide and/or tizoxanide formulations were administered orally with food to four healthy adult male volunteers to investigate each factor. Each of the volunteers received each of the six formulations in six different treatment periods, each treatment period being separated by at least one week. The formulations were administered orally with food. Blood samples were taken at eleven time points: immediately before the dose and at 1, 2, 3, 4, 5, 6, 7, 8, 10 and 12 hours post-dose. The following formulations were administered:

(1) an immediate-release ("IR") nitazoxanide/tizoxanide tablet containing 500 mg of 99% nitazoxanide/1% tizoxanide as active ingredient;

(2) an immediate-release tizoxanide tablet containing 500 mg of tizoxanide as active ingredient;

(3) an enteric-coated IR nitazoxanide/tizoxanide tablet coated with ACRYL-EZE® 70 mg (10% weight gain);

(4) a nitazoxanide/tizoxanide tablet containing 500 mg of 99% nitazoxanide, 1% tizoxanide as active ingredient, granulated in alcohol with hydroxypropylmethylcellulose (Metolose 90 SH) 100.000 SR as binding agent and dicalciumphosphate dihydrate as filler;

(5) a nitazoxanide/tizoxanide tablet containing 500 mg of 99% nitazoxanide, 1% tizoxanide as active ingredient, granulated in water with hydroxypropylmethylcellulose (Metolose 90 SH) 100.000 SR as binding agent and dicalciumphosphate dihydrate as filler; and (6) a nitazoxanide/tizoxanide tablet containing 450 mg of 99% nitazoxanide, 1% tizoxanide as active ingredient, granulated in water with hydroxypropylmethylcellulose (Methocel K100LV), 100 cP as binding agent and dicalciumphosphate dihydrate as filler (two tablets were administered to the patients).

Serum pharmacokinetic (PK) parameters were calculated from blood samples taken from the volunteers. Median values for $AUC_t$ (µg·hr/mL), $C_{max}$ (µg/mL), $C_{min}$ (µg/mL), and $T_{max}$ (hr) are presented in Table 1.

TABLE 1

Median serum pharmacokinetic parameter values for tizoxanide following administration of six different pharmaceutical formulations containing nitazoxanide and/or tizoxanide to four healthy adult male volunteers

| Formulation | $AUC_t$ μg*hr/mL | $C_{max}$ μg/mL | $C_{min}$ μg/mL | $T_{max}$ (hr) |
|---|---|---|---|---|
| (1) IR tablet, 500 mg[1] | 38.07 | 9.75 | 0.05 | 3 |
| (2) Tizoxanide, 500 mg[2] | 9.12 | 1.81 | 0.00 | 4 |
| (3) Enteric coated IR tablet, 500 mg[3] | 26.97 | 6.50 | 0.00 | 8 |
| (4) High-viscosity polymer (dry granulated), 500 mg[4] | 2.88 | 0.72 | 0.00 | 7 |
| (5) High-viscosity polymer 2 (wet granulated), 500 mg[5] | 6.14 | 1.49 | 0.00 | 8 |
| (6) Low-viscosity polymer (900 mg, 2 × 450 mg tablets)[6] | 34.77 | 7.03 | 0.21 | 7 |

[1] Standard immediate release tablet containing approximately 500 mg of active ingredient, which is 99% nitazoxanide/1% tizoxanide.
[2] Same formulation as IR tablet, except that active ingredient is 100% tizoxanide.
[3] IR tablet coated with ACRYL-EZE ® 70 mg (10% weight gain).
[4] 500 mg of active ingredient (99% nitazoxanide, 1% tizoxanide) granulated in alcohol with hydroxypropyl-methylcellulose (HPMC), 100,000 centipoise ("cP") (Metolose 90 SH 100.000 SR) as binding agent and dicalciumphosphate dihydrate as filler
[5] 500 mg of active ingredient (99% nitazoxanide, 1% tizoxanide) granulated in water with HPMC, 100,000 cP (Metolose 90 SH 100.000 SR) as binding agent and dicalciumphosphate dihydrate as filler
[6] 450 mg of active ingredient (99% nitazoxanide, 1% tizoxanide) granulated in water with HPMC, 100 cP (Methocel K100LV). Two tablets were administered to these patients.

Surprisingly, bioavailability was much lower following oral administration of tizoxanide (Formulation 2) compared to nitazoxanide (Formulation 1).

The enteric coating of the IR nitazoxanide/tizoxanide tablet (Formulation 3) delayed absorption in two patients as evidenced by the increase in $T_{max}$ from 3 to 8 hours, but it also prevented absorption in the other two patients.

The high-viscosity polymer (HPMC 100,000 cP) in Formulations 4 and 5 essentially prevented absorption.

Granulation in water using the high-viscosity polymer (Formulation 5) improved absorption compared to granulation in alcohol (Formulation 4).

Reduction of viscosity of HPMC to 100 cP (Formulation 6) resulted in a significant improvement in absorption ($AUC_t$), but absorption was still inferior to that of the IR tablet. Furthermore, even with delayed absorption and use of a higher 900 mg dose, tizoxanide was eliminated rapidly from serum so that the tizoxanide concentration in serum at 12 hours post-dose was below 2 μg/mL in all 4 patients (median 1.28 μg/mL).

Example 2

Bilayer Tablet Formulation

A bilayer tablet containing a total of 650 mg of nitazoxanide was made using standard formulation techniques, as described above. The composition of the bilayer tablet is presented in Table 2.

TABLE 2

Composition of Nitazoxanide 675 mg controlled release tablet.

| INGREDIENTS | Unit formula (mg/tablet) | Function | Reference to Standards* |
|---|---|---|---|
| Immediate Release Layer | | | |
| Nitazoxanide | 175 | Active substance | Monograph |
| Non-active substances: | | | |
| Maize starch | 36 | Diluent/disintegrant | Ph. Eur. 0344 |
| Hydroxypropylcellulose (Klucel EF) | 5 | Binder/suspending agent | Ph. Eur. 0337 |
| Sodium croscarmellose | 7.5 | Disintegrant | Ph. Eur. 0985 |
| Colloidal anhydrous silica (Aerosil 200) | 1 | Glidant | Ph. Eur. 0434 |
| Microcrystalline cellulose | 23 | Dry binder | Ph. Eur. 0316 |
| Magnesium stearate | 2.5 | Lubricant | Ph. Eur. 0229 |
| Water, Purified | 50 | Solvent | Ph. Eur. 0008 |
| Controlled Release Layer | | | |
| Nitazoxanide | 500 | Active substance | Monograph |
| Non-active substances: | | | |
| Hydroxypropyl-cellulose (Klucel EF) | 2.5 | Binder/suspending agent | Ph. Eur. 0337 |
| Hydroxypropyl-methylcellulose (Methocel E50LV) | 135 | Binder/suspending agent | Ph. Eur. 0348 |
| Dicalciumphosphate dihydrate (Emcompress) | 102.5 | Filler | Ph. Eur. 0116 |
| Colloidal anhydrous silica (Aerosil 200) | 3 | Glidant | Ph. Eur. 0434 |
| Magnesium stearate | 7 | Lubricant | Ph. Eur. 0229 |
| Water, Purified | 60 | Solvent | Ph. Eur. 0008 |
| Coating Materials | | | |
| OPADRY AMB 80W91416, GREEN (contains c.i. pigment blue 63, polyvinyl alcohol, talc, lecithins, xanthan gum, titanium dioxide, c.i. pigment yellow 42) | 40 | Coating | In house Monograph |

TABLE 2-continued

Composition of Nitazoxanide 675 mg controlled release tablet.

| INGREDIENTS | Unit formula (mg/tablet) | Function | Reference to Standards* |
|---|---|---|---|
| OPADRY FX 63F97546, Gloss (contains polyvinyl alcohol, talc, polyethylene glycol, mica-based pearlescent pigment, polysorbate 80) | 5 | Coating | In house Monograph |
| Water, Purified | 326 | Solvent | Ph. Eur. 0008 |

*References are to current editions.

Example 3

Batch Formulation of Bilayer Tablets

A batch of 100,000 nitazoxanide bilayer tablets (650 mg) of Example 2 was prepared as indicated in Table 3.

TABLE 3

Manufacturing batch formula for Nitazoxanide 675 mg controlled release tablets

| INGREDIENTS | Unit formula (mg/tablet) | Batch Formula (100,000 tablets) |
|---|---|---|
| Immediate Release Layer | | |
| Nitazoxanide | 175 | 17.5 kg |
| Non-active substances: | | |
| Maize starch | 36 | 3.6 kg |
| Hydroxypropylcellulose (Klucel EF) | 5 | 0.5 kg |
| Sodium croscarmellose | 7.5 | 0.75 kg |
| Colloidal anhydrous silica (Aerosil 200) | 1 | 0.1 kg |
| Microcrystalline cellulose | 23 | 2.3 kg |
| Magnesium stearate | 2.5 | 0.25 kg |
| Water, Purified | 50 | 5 kg |
| Controlled Release Layer | | |
| Nitazoxanide | 500 | 50 kg |
| Non-active substances: | | |
| Hydroxypropyl-cellulose (Klucel EF) | 2.5 | 0.25 kg |
| Hydroxypropyl-methylcellulose (Methocel E50LV) | 135 | 13.5 kg |
| Dicalciumphosphate dihydrate (Emcompress) | 102.5 | 10.25 kg |
| Colloidal anhydrous silica (Aerosil 200) | 3 | 0.3 kg |
| Magnesium stearate | 7 | 0.7 kg |
| Water, Purified | 60 | 6 kg |
| Coating Materials: | | |
| OPADRY AMB 80W91416, GREEN contains c.i. pigment blue 63, polyvinyl alcohol, talc, lecithins, xanthan gum, titanium dioxide, c.i. pigment yellow 42 | 40 | 4 kg |
| OPADRY FX 63F97546, Gloss (contains polyvinyl alcohol, talc, polyethylene glycol, mica-based pearlescent pigment, polysorbate 80) | 5 | 0.5 kg |
| Water, Purified | 326 | 32.6 kg |

The tablets were produced following the manufacturing protocol outlined below.

A. Equipment
   Frewitt sieve
   Collette Planetary blender
   Drying oven
   Tabletting machine—Manesty BB press
   Tablet deduster
   Coating apparatus—Accelacota
   All production equipment is cleaned prior to use.

B. Preparation of Immediate Release Granulate (Granulate A)
   1. The raw materials are weighed into sealed plastic bags.
   2. The integrity of the machine is checked before and after use.
   3. If necessary, the nitazoxanide and maize starch are sieved through a 1.25 mm mesh sieve using a Frewitt machine.
   4. These ingredients are transferred to the bowl of a Collette Planetary Blender and blended for 15 minutes at low speed.
   5. Dissolve hydroxypropylcellulose (HPC) in water, allow to stand overnight.
   6. This HPC solution is slowly added with mixing and the content is mixed for 5-10 minutes at low speed.
   7. If necessary, add extra water.
   8. The granulate is sieved through a 4 mm mesh sieve using a Frewitt machine, put on trays and dried at 50° C. for 12 to 16 hours.
   9. The trays are removed from the oven, samples are taken to test for loss on drying.
   10. The dried granulate is re-sieved through a 1.25 mm mesh sieve using a Frewitt machine and transferred to the drum of the blender.
   11. The aerosil, sodium croscarmellose and microcrystalline cellulose are sieved through a 1.25 mm mesh sieve using a Frewitt machine and added to the above and mixed for 15 minutes at low speed.
   12. Magnesium stearate is sieved through a 1.25 mm mesh sieve using a Frewitt machine and added to the above and mixed for 4 minutes at low speed.

C. Preparation of Controlled Release Granulate (Granulate B)
   1. The raw materials are weighed into sealed plastic bags.
   2. The integrity of the machine is checked before and after use.
   3. Nitazoxanide is transferred to the bowl of a Collette Planetary Blender.
   4. Dissolve HPC in water, allow to stand overnight.
   5. The HPC solution is slowly added with mixing and the content is mixed for 5-10 minutes at low speed.
   6. If necessary, add extra water.
   7. The granulate is sieved through a 4 mm mesh sieve using a Frewitt machine, put on trays and dried at 50° C. for 12 to 16 hours.
   8. The trays are removed from the oven, samples are taken to test for loss on drying.
   9. The dried granulate is re-sieved through a 1.25 mm mesh sieve using a Frewitt machine and transferred to the drum of the blender.
   10. Hydroxypropylmethylcellulose, dicalciumphosphate dihydrate and aerosil are sieved through a 1.25 mm mesh sieve using a Frewitt machine.
   11. These ingredients are added to the bowl of the Colette Planetary Blender and blended for 15 minutes at low speed.

12. Magnesium stearate is sieved through a 1.25 mm mesh sieve using a Frewitt machine and added to the above and mixed for 4 minutes at low speed.

D. Tabletting
1. The tabletting is carried out using a Manesty BB press tabletting machine (19 mm oblong biconvex punch).
2. Filling and precompression of granulate B: target weight=750 mg second filling with granulate A: target weight=250 mg and final compression: final weight=1000 mg The pressure is adjusted after visual inspection.
1. The tablets are dedusted.
2. Tablets are taken for weight control, friability, assay, thickness and hardness.
3. The gross and net weight of tablets produced is recorded. If these are not within ±5% of limits, reasons for losses must be recorded.

E. Coating
1. Verify the identity of the material used for manufacturing and the line clearance.
2. The tablets are transferred to the coating apparatus (Accelacota).
3. Prepare the coating suspension as follows:
Transfer purified water into a suitable container.
Disperse the OPADRY AMB 80W91416, GREEN by means of rapid stirring.
After all the OPADRY has been added, continue stirring for a further 45 minutes.
4. Pour the coating suspension into the coating apparatus (Accelacota).
5. Mix gently while the coating suspension is being sprayed.
6. Repeat step 32-34 with OPADRY FX 63F97546, Gloss.
7. Afterwards, verify the weight increase of 100 tablets. The increase must be at least 35 mg/tablet.
8. Sampling and control of unit weight and disintegration.
9. After approval by Quality Assurance, transfer the tablets into clean containers, lined with two polyethylene bags.

Example 4

Testing of Final Bilayer Tablets

The 675 mg nitazoxanide bilayer tablet described in Examples 2 and 3 ("NTZ 675 mg tablet") was tested in the following two clinical studies.
1. Study RM06-1001 (Pharmacokinetics and Tolerability Study in Healthy Volunteers Using 675 Mg Controlled Release Tablets).

12 healthy adult volunteers were randomized in double-blind fashion to receive one NTZ 675 mg tablet and one placebo tablet b.i.d. or two NTZ 675 mg tablets b.i.d. for 7 days. After a 7-day washout period, each subject crossed over to receive 7 days of treatment with the dose that he had not received during the first 7-day treatment period. Plasma samples were collected for assay of NTZ metabolites, tizoxanide (T) and tizoxanide glucuronide (TG), over 12 hours following the first dose on day 1, before the morning dose on day 5 and day 6 and over 24 hours following the morning dose on day 7 (the last dose).

The following table presents important pharmacokinetic parameters for tizoxanide obtained after 7 days administration of the controlled release tablets compared to results obtained from a similar study using the nitazoxanide 500 mg immediate release ("IR") tablet (Study 198.637). The total exposure (AUC) and minimum plasma concentrations ($C_{min}$) were significantly higher for the controlled release tablet than for the IR tablet, but the maximum plasma concentrations were similar.

TABLE 4

Comparison of Important Pharmacokinetics Parameters for Tizoxanide from Study RM06-1001 to Historical Data from a Similar Study of the Nitazoxanide 500 mg Immediate Release Tablets

|  | CR Tablet | | IR Tablet | |
| --- | --- | --- | --- | --- |
|  | 675 mg b.i.d. (n = 12) | 1350 mg b.i.d. (n = 11) | 500 mg b.i.d. (n = 6) | 1000 mg b.i.d. (n = 5) |
| $AUC_\infty$ (μg · h/mL) | 78.3 | 221 | 52.3 | 158 |
| $C_{min}$ (μg/mL) | 1.26 | 5.39 | 0.40 | 2.14 |
| $C_{max}$ (μg/mL) | 11.9 | 29.8 | 9.3 | 24.4 |

The values presented in Table 4 are arithmetic means. Data for CR tablet were taken from study RM06-1001. Data for IR tablet was taken from study 198.637. In both studies, the tablets were administered b.i.d. with food for 7 days in healthy adult male volunteers. The pharmacokinetic parameters presented are for day 7 of b.i.d. dosing.

Only mild to moderate adverse events were observed in Study RM06-1001, the most common being chromaturia, fatigue, diarrhea, conjunctival discoloration, abdominal pain and nausea. Adverse events occurring with greater frequency during the high dose treatment were: diarrhea (8 [73%] versus 4 [33%] subjects), nausea (7 [64%] versus 3 [25%] subjects), abdominal pain (6 [55%] versus 2 [17%] subjects), and decreased appetite (4 [36%] versus 1 [8%] subjects). The occurrence rates of all other adverse events were similar for the two treatment regimens. There were no significant changes in clinical laboratory values, vital signs or ECG parameters.

Historically, the most common adverse events associated with oral administration of nitazoxanide have been related to the gastrointestinal tract. The following table presents the most common gastrointestinal adverse events reported from Study RM06-1001 alongside those reported in Study 198.637 using the 500 mg immediate release (IR) tablet. The data in Table 5 indicate that the controlled release tablet is better tolerated than the immediate release tablet.

TABLE 5

Comparison of Numbers of Patients Reporting Most Common Gastrointestinal Adverse Events from Phase I Clinical Studies in Healthy Male Volunteers: Studies RM06-1001 and 198.637

|  | Placebo IR Tablet BID (n = 4) [1] | CR Tablet 675 mg BID (n = 12) [2] | IR Tablet 500 mg BID (n = 6) [1] | CR Tablet 1350 mg BID (n = 11) [2] | IR Tablet 1000 mg BID (n = 6) [1] |
| --- | --- | --- | --- | --- | --- |
| Abdominal pain | 1, 25% | 2, 17% | 3, 50% | 6, 55% | 6, 100% |
| Diarrhea | 2, 50% | 4, 33% | 4, 67% | 8, 73% | 5, 83% |

TABLE 5-continued

Comparison of Numbers of Patients Reporting Most Common Gastrointestinal Adverse Events from Phase I Clinical Studies in Healthy Male Volunteers: Studies RM06-1001 and 198.637

|  | Placebo IR Tablet BID (n = 4) [1] | CR Tablet 675 mg BID (n = 12) [2] | IR Tablet 500 mg BID (n = 6) [1] | CR Tablet 1350 mg BID (n = 11) [2] | IR Tablet 1000 mg BID (n = 6) [1] |
|---|---|---|---|---|---|
| Flatulence | 2, 50% | 0, 0% | 1, 17% | 0, 0% | 4, 67% |
| Nausea | 0, 0% | 3, 25% | 0, 0% | 7, 64% | 4, 67% |
| Total | 5 | 9 | 8 | 21 | 21 |
| Total/n | 1.25 | 0.75 | 1.25 | 1.91 | 3.5 |
| Moderate AEs[3] | 0, 0% | 0, 0% | 0, 0% | 4, 37% | 3, 50% |
| Discontinuations[4] | 0, 0% | 0, 0% | 0, 0% | 0, 0% | 1, 17% |

[1] From study 198.637.
[2] From study RM06-1001.
[3] All other adverse events were mild.
[4] Discontinuations due to adverse events.

Data for the CR tablet was taken from study RM06-1001 (final report in preparation). Data for the IR tablet and the placebo tablets were taken from study 198.637. In both studies, the tablets were administered b.i.d. with food for 7 days in healthy adult male volunteers. Both studies were conducted at the same clinical center by SGS Biopharma (CRO), and both studies were double-blinded so that neither the patients or physicians were aware of treatment group assignment. The study of the IR tablet was conducted in 1998, and the study of the CR tablet was conducted in 2008.

2. Study RM06-1002 (Viral Kinetics Study in Patients with Chronic Hepatitis C Genotype 4 Using 675 Mg Controlled Release Tablets).

40 interferon-naïve patients with chronic hepatitis C genotype 4 were randomized (2:2:1) in double-blind fashion to receive NTZ 675 mg b.i.d. for 4 weeks followed by NTZ 675 mg b.i.d.+PegIFN+RBV for 48 weeks, NTZ 1350 mg b.i.d. for 4 weeks followed by NTZ 1350 mg b.i.d.+PegIFN+RBV for 48 weeks, or placebo b.i.d. for 4 weeks followed by placebo+PegIFN+RBV for 48 weeks. Dosing of PegIFN (peginterferon alfa-2a, Pegasys®, Roche, Basel, Switzerland) was 180 µg/week, and dosing of RBV (Viracure®, October Pharma, Cairo, Egypt) was 1000 mg/day (weight <75 kgs), or 1200 mg/day (body weight≥75 kgs). HCV RNA was quantified at baseline and on days 3, 7, 14 and 28 during the monotherapy lead-in phase and on days 3, 7, 14 and 28 of the combination therapy phase. The primary endpoint was the change in quantitative HCV RNA from baseline to week 4 of combination therapy. Secondary endpoints included RVR (HCV RNA <12 IU/mL after 4 weeks of combination therapy), cEVR (HCV RNA <12 IU/mL after 12 weeks of combination therapy) and EVR ($\geq 2 \log_{10}$ drop in HCV RNA after 12 weeks of combination therapy). HCV RNA was quantified using the Abbott Realtime HCV RT-PCR assay (LOD=12 IU/mL)

Virologic response through study week 16 is described in the table below.

TABLE 6

Virologic Response to Treatment Using Controlled Release Tablets

|  | 1350 mg BID + PEG + RBV (n = 16) | 675 mg BID + PEG + RBV (n = 17) | Placebo + PEG + RBV (n = 8) |
|---|---|---|---|
| Mean reduction of HCV RNA from baseline to week 4 of combination therapy (log10 IU/mL) | −4.4 | −3.9 | −3.5 |

TABLE 6-continued

Virologic Response to Treatment Using Controlled Release Tablets

|  | 1350 mg BID + PEG + RBV (n = 16) | 675 mg BID + PEG + RBV (n = 17) | Placebo + PEG + RBV (n = 8) |
|---|---|---|---|
| RVR | 10 (63%) | 10 (59%) | 4 (50%) |
| cEVR | 16 (100%) | 14 (82%) | 5 (63%) |
| EVR | 16 (100%) | 15 (88%) | 5 (63%) |

No serious adverse events were reported, and no patients discontinued treatment due to an adverse event.

This study demonstrated a dose-related improvement in virologic response to therapy. In a previous study in patients with chronic hepatitis C genotype 4 who were treated with the IR tablet twice daily plus peginterferon alfa-2a and ribavirin, the proportion of patients achieving undetectable levels of HCV RNA after 12 weeks of combination therapy (cEVR) was 86% (24/28). Use of the new controlled release tablet formulation with fewer side effects allowed us to increase the dose of active ingredient to 1350 mg twice daily, improving the concentrations of tizoxanide in plasma and improving the proportion of patients achieving cEVR.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of reducing one or more side-effects associated with treatment with nitazoxanide or tizoxanide in a patient, the method comprising administering to the patient a therapeutically effective amount of a pharmaceutical composition in the form of a solid dosage form, the composition comprising (a) a first portion comprising a first quantity of nitazoxanide, tizoxanide or a pharmaceutically acceptable salt or ester thereof in a controlled release formulation; and (b) a second portion comprising a second quantity of nitazoxanide, tizoxanide or a pharmaceutically acceptable salt or ester thereof in an immediate release formulation, wherein the one or more side effects is selected from abdominal pain, diarrhea, flatulence and nausea.

2. The method of claim 1, wherein the first and second quantities of nitazoxanide, tizoxanide or a pharmaceutically acceptable salt or ester thereof are each nitazoxanide.

3. The method of claim 2, wherein the first portion further comprises a low viscosity polymer.

4. The method of claim 2, wherein the ratio of the first quantity of nitazoxanide to the second quantity of nitazoxanide is about 2.5:1 to about 4:1.

5. The method of claim 2, wherein
the first quantity of nitazoxanide comprises about 500 mg of nitazoxanide; and
the second quantity of nitazoxanide comprises about 175 mg of nitazoxanide in an immediate release formulation.

6. The method of claim 2, wherein the solid dosage form is a bilayer tablet wherein:
the first portion (a) forms a first layer comprising about 500 mg of nitazoxanide in a controlled release formulation, and further comprising a low-viscosity hydroxypropylmethylcellulose;
the second portion (b) forms a second layer comprising about 175 mg of nitazoxanide in an immediate release formulation, the second layer deposited on top of and compressed with the first layer to form a core tablet.

7. The method of claim 6, wherein the tablet further comprises an outer coating (c) applied to the core tablet.

8. The method of claim 2, wherein the solid oral dosage form is a tablet.

9. The method of claim 2, wherein the solid oral dosage form is a capsule.

10. The method of claim 9, wherein the first portion (a) is in the form of controlled-release granules containing the first quantity of nitazoxanide, and the second portion (b) is in the form of immediate-release granules containing the second quantity of nitazoxanide.

11. A method for increasing the bioavailability of nitazoxanide or an analogue thereof in a patient, the method comprising administering to the patient a therapeutically effective amount of a pharmaceutical composition in the form of a solid dosage form, the composition comprising (a) a first portion comprising a first quantity of nitazoxanide, tizoxanide or a pharmaceutically acceptable salt or ester thereof in a controlled release formulation; and (b) a second portion comprising a second quantity of nitazoxanide, tizoxanide or a pharmaceutically acceptable salt or ester thereof in an immediate release formulation.

12. The method of claim 11, wherein the first and second quantities of nitazoxanide, tizoxanide or a pharmaceutically acceptable salt or ester thereof are each nitazoxanide.

13. The method of claim 12, wherein the first portion further comprises a low viscosity polymer.

14. The method of claim 12, wherein the ratio of the first quantity of nitazoxanide to the second quantity of nitazoxanide or an analogue thereof is about 2.5:1 to about 4:1.

15. The method of claim 12, wherein
the first quantity of nitazoxanide comprises about 500 mg of nitazoxanide; and
the second quantity of nitazoxanide comprises about 175 mg of nitazoxanide in an immediate release formulation.

16. The method of claim 12, wherein the solid dosage form is a bilayer tablet wherein:
the first portion (a) forms a first layer comprising about 500 mg of nitazoxanide in a controlled release formulation, and further comprising a low-viscosity hydroxypropylmethylcellulose;
the second portion (b) forms a second layer comprising about 175 mg of nitazoxanide in an immediate release formulation, the second layer deposited on top of and compressed with the first layer to form a core tablet.

17. The method of claim 16, wherein the tablet further comprises an outer coating (c) applied to the core tablet.

18. The method of claim 12, wherein the solid oral dosage form is a tablet.

19. The method of claim 12, wherein the solid oral dosage form is a capsule.

20. The method of claim 19, wherein the first portion (a) is in the form of controlled-release granules containing the first quantity of nitazoxanide, and the second portion (b) is in the form of immediate-release granules containing the second quantity of nitazoxanide.

\* \* \* \* \*